United States Patent
Tischer et al.

(10) Patent No.: US 11,476,605 B2
(45) Date of Patent: Oct. 18, 2022

(54) INTERCONNECT DEVICE AND MODULE USING SAME

(71) Applicant: Qorvo Biotechnologies, LLC, Plymouth, MN (US)

(72) Inventors: John Mark Tischer, Waseca, MN (US); Christopher Jennings Madsen, Waseca, MN (US); Roger Paul Mann, Waseca, MN (US)

(73) Assignee: Qorvo Biotechnologies, LLC, Plymouth, MN (US)

( * ) Notice: Subject to any disclaimer, the term of this patent is extended or adjusted under 35 U.S.C. 154(b) by 625 days.

(21) Appl. No.: 14/893,408

(22) PCT Filed: May 23, 2014

(86) PCT No.: PCT/US2014/039294
§ 371 (c)(1),
(2) Date: Nov. 23, 2015

(87) PCT Pub. No.: WO2014/190240
PCT Pub. Date: Nov. 27, 2014

(65) Prior Publication Data
US 2016/0172775 A1 Jun. 16, 2016

Related U.S. Application Data

(60) Provisional application No. 61/826,941, filed on May 23, 2013.

(51) Int. Cl.
*H01R 12/72* (2011.01)
*G01N 29/02* (2006.01)
(Continued)

(52) U.S. Cl.
CPC ......... *H01R 12/721* (2013.01); *G01N 29/022* (2013.01); *G01N 29/036* (2013.01);
(Continued)

(58) Field of Classification Search
CPC .. H01R 12/721; G01N 29/022; G01N 29/036; G01N 29/222; G01N 29/30;
(Continued)

(56) References Cited

U.S. PATENT DOCUMENTS 2,136,612 A 11/1938 Dubuar
2,881,273 A 4/1959 Shaler
(Continued)

FOREIGN PATENT DOCUMENTS

EP 1 830 169 A1 9/2007
WO WO 2006/010206 A1 2/2006
(Continued)

OTHER PUBLICATIONS

PICMG® AMC.0 R2.0 Short Form Specification; Available Online: https://www.picmg.org/wp-content/uploads/AMC.0_R2.0_Short_Form.pdf; Dec. 28, 2006; p. 1-56. (Year: 2006).*
(Continued)

*Primary Examiner* — Robert J Eom
(74) *Attorney, Agent, or Firm* — Haynes Boone, LLP; Benjamin C. Pelletier; Destiny L. Stephenson

(57) ABSTRACT

Various embodiments of an interconnect device and modules and systems that utilize such interconnect device are disclosed. In one or more embodiments, the interconnect device can include a printed circuit board (PCB). The PCB can include a substrate forming a resiliently deflectable element, a conductive material disposed on the substrate, and an electrical contact disposed on the resiliently deflectable element and electrically coupled to the conductive material. The interconnect device can also include a connector that includes a connecting pin configured to electrically couple with the electrical contact of the resiliently deflectable
(Continued)

element of the PCB and cause the resiliently deflectable element to deflect when the element contacts the connecting pin.

20 Claims, 6 Drawing Sheets

(51) Int. Cl.
| | |
|---|---|
| *G01N 29/30* | (2006.01) |
| *G01N 29/22* | (2006.01) |
| *H05K 1/11* | (2006.01) |
| *G01N 29/036* | (2006.01) |
| *G01N 33/543* | (2006.01) |
| *H01L 41/08* | (2006.01) |
| *H03H 9/54* | (2006.01) |
| *H05K 1/18* | (2006.01) |

(52) U.S. Cl.
CPC ........... *G01N 29/222* (2013.01); *G01N 29/30* (2013.01); *G01N 33/54373* (2013.01); *H01L 41/081* (2013.01); *H01L 41/0825* (2013.01); *H03H 9/54* (2013.01); *H05K 1/118* (2013.01); *G01N 2291/014* (2013.01); *G01N 2291/022* (2013.01); *G01N 2291/0255* (2013.01); *G01N 2291/0256* (2013.01); *G01N 2291/0426* (2013.01); *H05K 1/184* (2013.01); *H05K 2201/09063* (2013.01); *H05K 2201/10068* (2013.01); *H05K 2201/10151* (2013.01)

(58) Field of Classification Search
CPC ........... G01N 33/54373; H01L 41/081; H01L 41/0825; H03H 9/54; H05K 1/118
See application file for complete search history.

(56) References Cited

U.S. PATENT DOCUMENTS

| | | | |
|---|---|---|---|
| 2,951,218 A | 8/1960 | Arditi | |
| 4,634,195 A | 1/1987 | Shoemaker | |
| 4,795,354 A * | 1/1989 | Owen | H01R 12/87 439/135 |
| 4,895,524 A * | 1/1990 | Thepault | H01R 12/62 361/749 |
| 5,554,042 A | 9/1996 | Denninger | |
| 5,910,522 A | 6/1999 | Schmidt et al. | |
| 5,932,953 A | 8/1999 | Drees et al. | |
| 6,055,448 A | 4/2000 | Anderson et al. | |
| 6,093,059 A | 7/2000 | Bogese | |
| 6,237,417 B1 | 5/2001 | Lonsdale et al. | |
| 6,467,351 B2 | 10/2002 | Lonsdale et al. | |
| 6,551,128 B2 | 4/2003 | Asai | |
| 6,623,307 B2 | 9/2003 | Korsunskey et al. | |
| 6,935,868 B1 * | 8/2005 | Campini | G06F 1/186 361/748 |
| 7,349,223 B2 | 3/2008 | Haemer et al. | |
| 7,563,128 B2 | 7/2009 | Suzuki et al. | |
| 7,621,761 B2 | 11/2009 | Mok et al. | |
| 7,690,923 B2 | 4/2010 | Horchler et al. | |
| 7,721,590 B2 | 5/2010 | Kolosov et al. | |
| 7,933,123 B2 | 4/2011 | Wang et al. | |
| 8,178,047 B2 | 5/2012 | Wang et al. | |
| 8,333,619 B2 | 12/2012 | Kondo et al. | |
| 8,346,482 B2 | 1/2013 | Fernandez | |
| 8,409,875 B2 | 4/2013 | Johal et al. | |
| 8,441,081 B2 | 5/2013 | Arora et al. | |
| 2002/0123270 A1 | 9/2002 | Belopolsky | |
| 2002/0178789 A1 * | 12/2002 | Sunshine | G01N 29/022 73/31.06 |
| 2003/0101006 A1 | 5/2003 | Mansky et al. | |
| 2005/0042931 A1 | 2/2005 | Lavie | |
| 2005/0227508 A1 | 10/2005 | Syms | |
| 2006/0134362 A1 | 6/2006 | Lu et al. | |
| 2006/0242828 A1 | 11/2006 | Kirby et al. | |
| 2009/0101274 A1 * | 4/2009 | Olson | H05K 3/002 156/182 |
| 2010/0068933 A1 | 3/2010 | Ikegami et al. | |
| 2011/0130048 A1 | 6/2011 | Haunberger et al. | |
| 2011/0143601 A1 | 6/2011 | Katsui et al. | |
| 2011/0190615 A1 | 8/2011 | Phillips et al. | |
| 2012/0100636 A1 | 4/2012 | Johal et al. | |
| 2012/0330179 A1 | 12/2012 | Yuk et al. | |
| 2013/0018250 A1 | 1/2013 | Caprio et al. | |
| 2013/0018251 A1 | 1/2013 | Caprio et al. | |
| 2013/0045474 A1 | 2/2013 | Rozmyslowicz et al. | |
| 2013/0084716 A1 | 4/2013 | Namjoshi et al. | |
| 2013/0102199 A1 | 4/2013 | Venaleck et al. | |
| 2013/0105984 A1 | 5/2013 | Rathburn | |

FOREIGN PATENT DOCUMENTS

| | | |
|---|---|---|
| WO | WO 2006/026036 A1 | 3/2006 |
| WO | WO 2014/190238 A1 | 11/2014 |
| WO | WO 2014/190295 A3 | 11/2014 |

OTHER PUBLICATIONS

European Patent Application No. 14801041.6, filed May 23, 2014; Supplementary Search Report dated Nov. 16, 2016; 10 pages.
International Search Report / Written Opinion dated Sep. 30, 2014, International Application No. PCT/US2014/039291, filed May 23, 2014; 10 pages.
Sauerbrey, *Zeitschrift für Physik*, 155(2):206-222.
International Search Report / Written Opinion dated Sep. 30, 2014, Application No. PCT/US2014/039294, filed May 23, 2014; 10 pages.
International Preliminary Report on Patentability dated Dec. 3, 2015 International Application No. PCT/US2014/039291, filed May 23, 2014; 8 pgs.
International Preliminary Report on Patentability dated Dec. 3, 2015, International Application No. PCT/US2014/039294, filed May 23, 2014; 8 pgs.

* cited by examiner

INTERCONNECT DEVICE AND MODULE USING SAME

This application is a U.S. National Stage Application of International Application. No. PCT/US2014/039294, titled INTERCONNECT DEVICE AND MODULE USING SAME, filed on May 23, 2014, which claims the benefit of U.S. Provisional Application No. 61/826,941 filed May 23, 2013, entitled RESONATOR ASSEMBLY HAVING DEFLECTABLE INTERCONNECT ELEMENT, the disclosures of which are incorporated by reference herein in their entirety.

BACKGROUND

Piezoelectric devices such as thin film bulk acoustic resonators (TFBAR) and similar technologies like quartz crystal microbalances (QCM) have been employed as mass detectors for some time. One application of piezoelectric resonators is in detecting very small quantities of materials. Piezoelectric resonators used as sensors in such applications are sometimes called "micro-balances." A piezoelectric resonator is typically constructed as a thin, planar layer of crystalline or polycrystalline piezoelectric material sandwiched between two electrode layers. When used as a sensor, the resonator is exposed to the material being detected to allow the material to bind on a surface of the resonator.

The material to be detected is often an analyte. A binding partner (e.g., an antibody, etc.) that selectively binds the analyte may be immobilized relative to a surface of the resonator. When the analyte is contacted with the surface of the resonator, the mass on the surface increases. The changed mass results in changes to the resonance phase, frequency, etc., of the resonator.

One conventional way of detecting the amount of the material bound on the surface of a resonator is to operate the resonator as an oscillator at its resonant frequency. As the material being detected binds on the resonator surface, the oscillation frequency of the resonator is reduced. This change in the oscillation frequency of the resonator, presumably caused by the binding of the material on the resonator surface, is measured and used to calculate the amount of the material bound on the resonator or the rate at which the material accumulates on the resonator's surface.

The sensitivity of a piezoelectric resonator in air as a material sensor is theoretically proportional to the square of the resonance frequency. See, e.g., G. Sauerbrey, *Zeitschrift für Physik* 155 (2): 206-222. Thus, the sensitivities of material sensors based on the popular quartz crystal resonators are limited by their relatively low oscillating frequencies, which typically range from several MHz to about 100 MHz. The development of thin-film resonator (TFR) technology can potentially produce sensors with significantly improved sensitivities. A thin-film resonator can be formed by depositing a thin film of piezoelectric material, such as AlN or ZnO, on a substrate. Due to the small thickness of the piezoelectric layer in a thin-film resonator, which is on the order of several microns, the resonant frequency of the thin-film resonator is on the order of 1 GHz. The high resonant frequencies and the corresponding high sensitivities make thin-film resonators useful for material sensing applications.

Regardless of the technology employed, electrical connections associated with piezoelectric resonator analyte measurement systems should be sufficiently robust. Often such systems contain a module or cartridge that includes the resonator and other circuitry and an associated instrument or apparatus that can receive the module or a portion thereof and that can operably couple to the resonator when the module is received by the associated apparatus. The associated apparatus may include any suitable or desirable electrical components, such as a power supply, processor, memory, signal generator, and associated circuitry (e.g., for producing a resonance wave), detection components and associated circuitry (e.g., for detecting changes to the wave as a result of analyte binding), etc. The memory may contain computer readable instructions that cause the associated instrument to generate a wave and detect changes in the wave. Examples of suitable circuitry and associated devices are described in U.S. Pat. Nos. 5,932,953 and 8,409,875, each of which is hereby incorporated herein by reference in their respective entireties to the extent that they do not conflict with the present disclosure.

SUMMARY

In general, the present disclosure provides various embodiments of an interconnect device, and modules and systems that utilize such device.

In one aspect, the present disclosure provides an interconnect device that includes a printed circuit board (PCB). The PCB can include a substrate that forms a resiliently deflectable element, a conductive material disposed on the substrate, and an electrical contact disposed on the resiliently deflectable element and electrically coupled to the conductive material. The interconnect device further includes a connector that includes a connecting pin configured to electrically couple with the electrical contact of the resiliently deflectable element of the PCB and cause the resiliently deflectable element to deflect when the element contacts the connecting pin.

In another aspect, the present disclosure provides a resonator sensor module that includes a module interface and a resonator electrically coupled to the module interface. The module interface includes a printed circuit board (PCB) that includes a substrate that forms a resiliently deflectable element, a conductive material disposed on the substrate, and an electrical contact disposed on the resiliently deflectable element and electrically coupled to the conductive material. The resonator is electrically coupled to the conductive material.

In one or more embodiments, the resonator sensor module can be included in a resonator sensor system for measuring binding kinetics of an interaction of an analyte material present in a fluid sample. The system also includes a measurement apparatus operatively coupled to the resonator sensor module through an interconnect device that includes the module interface of the resonator sensor module and a connector of the measurement apparatus. The measurement apparatus includes actuation circuitry configured to drive the resonator into an oscillating motion, measurement circuitry configured to measure a resonator output signal representing a resonance characteristic of the oscillating motion of the resonator, and a controller operatively coupled to the actuation and measurement circuitry.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

In general, the present disclosure provides various embodiments of an interconnect device and modules and systems that utilize such device. In one or more embodiments, the interconnect device can include a printed circuit board (PCB) and a connector that is configured to electrically couple with the PCB. Further, in one or more embodiments, the PCB includes a substrate that forms a resiliently deflectable element, a conductive material disposed on the substrate, and an electrical contact disposed on the resiliently deflectable element and electrically coupled to the conductive material. The connector can, in one or more embodiments, include a connecting pin configured to electrically couple with the electrical contact of the resiliently deflectable element of the PCB and cause the resiliently deflectable element to deflect when the element contacts the connecting pin. The resilient nature of the deflectable element results in force being applied by the connecting pin to the deflectable element. In one or more embodiments, the force is sufficient to cause a robust electrical connection between the contact of the deflectable element and the connecting pin. In one or more embodiments, it has been found that by forming "fingers" from the circuit board to form resiliently deflectable elements, sufficiently robust electrical connection may be made between the contacts of the resiliently deflectable elements and the associated apparatus. Such "fingers" or resiliently deflectable elements may be formed by slots or slits in the PCB.

As indicated herein, one or more sensors (e.g., resonators) may be associated with a PCB. The sensor may be operably coupled with the conductive material of the PCB.

Any suitable PCB can be used to form one or more resiliently deflectable elements having one or more contacts. In one or more embodiments, the PCB includes one or more non-conductive substrates onto which electrical components, conductive traces, contact pads or the like are disposed. The conductive traces, contact pads, etc. may be formed in sheets that are laminated onto a non-conductive substrate or may be disposed on the substrate in any other suitable manner. Conductive materials on one side of a substrate may be connected to conductive materials on another side of the substrate through vias or through-holes formed in the substrate. If the PCB includes multiple layers, conductive materials disposed on one layer may be coupled to conductive materials on another layer through vias.

Figure 1:
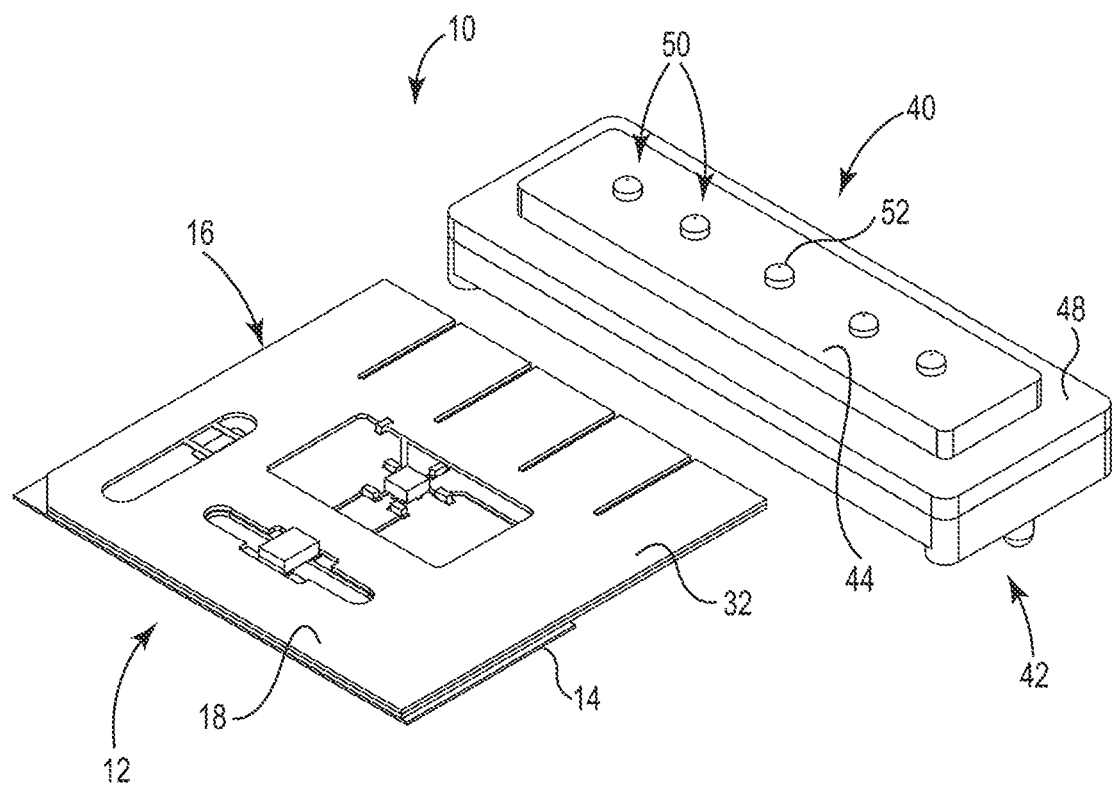
FIG. 1 is a schematic perspective view of one embodiment of an interconnect device.

For example, FIG. 1 is a schematic perspective view of one embodiment of an interconnect device 10. As illustrated in FIG. 1, the interconnect device 10 includes a printed circuit board (PCB) 12 and a connector 40. Any suitable PCB 12 and connector 40 can be utilized in the interconnect device 10.

In one or more embodiments, the interconnect device 10 can provide a durable connection that allows for two or more apparatuses, components, devices, or systems to be connected and disconnected multiple times without compromising the integrity of the electrical coupling between the apparatuses. Any suitable apparatuses, components, devices, and systems can be electrically coupled utilizing the interconnect device 10 as is further described herein. In one or more embodiments, the device 10 can provide a sealed connection between components to prevent exposure of the connection and internal circuitry of the components to various environmental elements, e.g., moisture, dirt, etc. Any suitable technique or combinations of techniques can be utilized to protect the interconnect device from the external environment.

The interconnect device 10 can be disposed within one or more components in any suitable configuration. For example, in one or more embodiments, the PCB 12 can be disposed within a case or enclosure of one component and the connector 40 can be disposed within a case or enclosure of another component.

The PCB 12 can include any PCB. For example, FIG. 4 is a schematic plan view of a first major surface 18 of a substrate 14 of the PCB 12 of FIG. 1, and FIG. 5 is a schematic plan view of a second major surface 20 of the substrate 14 of PCB 12.

The PCB 12 includes the substrate 14. The substrate 14 can include any suitable material or combination of materials. In one or more embodiments, the substrate can include electrically insulating materials.

The substrate 14 forms resiliently deflectable elements 16. As used herein, the phrase "resiliently deflectable element" refers to one or more elements formed by the substrate of the PCB that can be deflected one or more times by a connector to provide an electrical coupling between the PCB and the connector and return to their original configurations and/or shapes when the elements are no longer deflected by the connector. The resiliently deflectable elements 16 can be formed using any suitable technique or combination of techniques.

Figure 4:
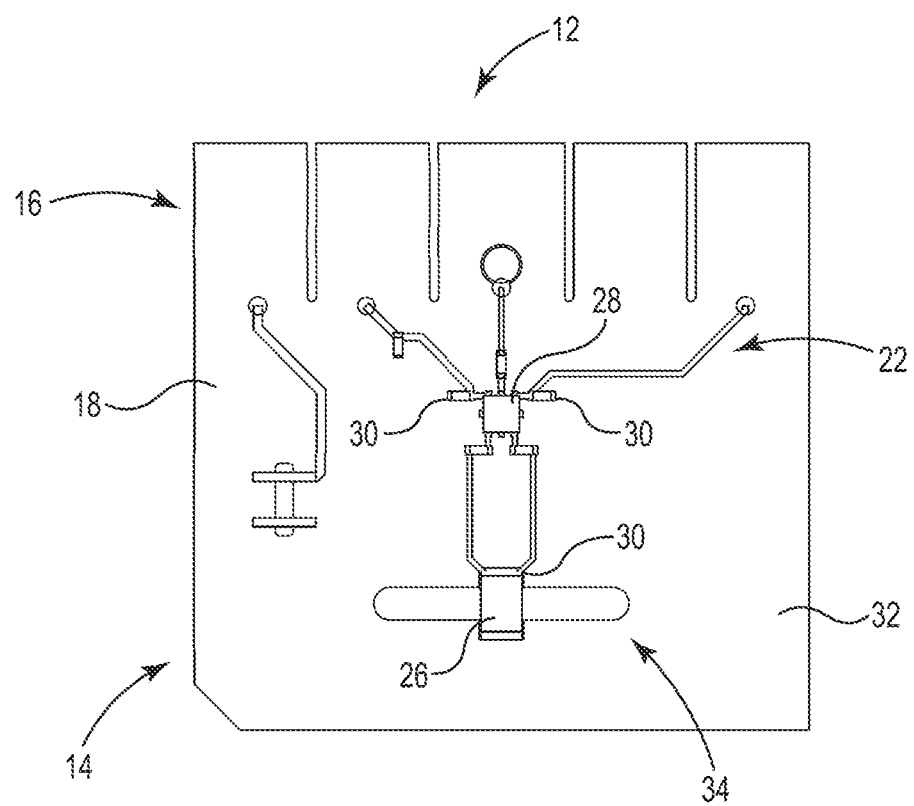
FIG. 4 is a schematic plan view of a first major surface of a printed circuit board (PCB) of the interconnect device of FIG. 1.
Figure 5:
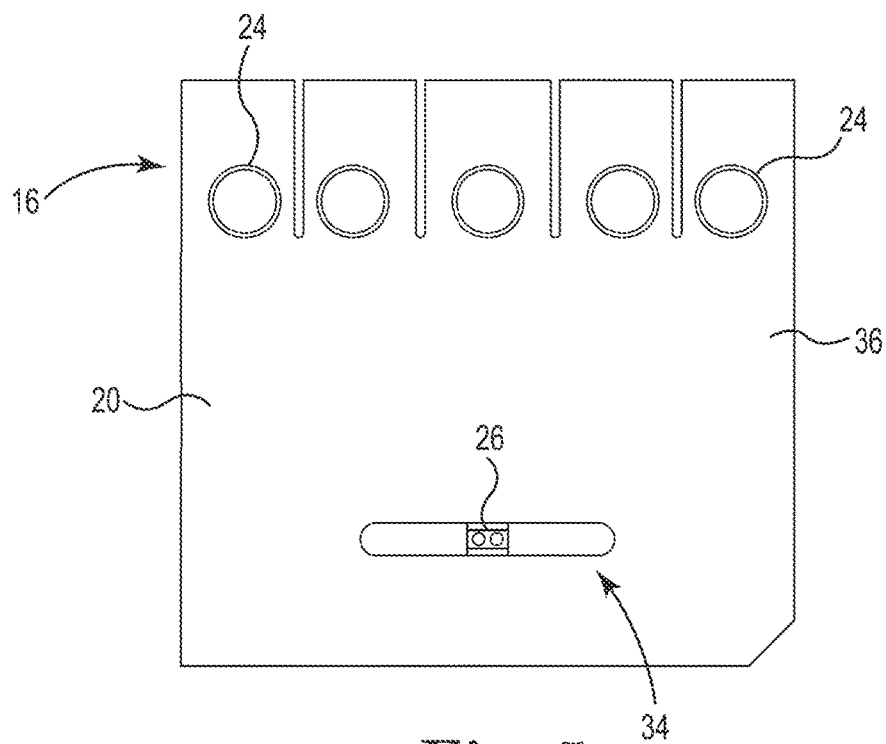
FIG. 5 is schematic plan view of a second major surface of the PCB of the interconnect device of FIG. 1.

Although FIGS. 1 and 4-5 illustrate that PCB 12 includes 5 resiliently deflectable elements 16, the PCBs of the disclosure can include any suitable number of resiliently deflectable elements, e.g., 1, 2, 3, 4, 5, or more resiliently deflectable elements.

Each resiliently deflectable element 16 can provide one more electrical connections or pathways between the PCB 12 and an associated apparatus. For example, in one or more embodiments, each resiliently deflectable element 16 can provide a discrete channel or pathway between the PCB 12 and an associated apparatus via the connector 40. As used herein, a channel refers to a discrete electronic pathway through which data or electrical signals may be transmitted.

Further, each resiliently deflectable element 16 can include any suitable dimension and shape or combination of shapes. For example, as illustrated, each resiliently deflectable element 16 has taken a substantially rectangular shape. In one or more embodiments, the resiliently deflectable elements 16 can take a substantially square shape, a curvilinear shape, etc. The resiliently deflectable elements 16 can also have any suitable spacing between each element. Alternatively, in one or more alternative embodiments, one or more resiliently deflectable elements 16 can be connected to an adjacent element so that there is no space between such elements.

Disposed on the substrate 14 is conductive material 22. Any suitable material or combination of materials can be utilized for conductive material 22. In one or more embodiments, the conductive material 22 may be electrically conductive such that an electrical connection can be provided between various components or devices disposed on the PCB 12 and the connector 40 as is further described herein. In one or more embodiments, the conductive material 22 is shaped or formed to provide conductive traces or transmission lines between various components or devices provided on or associated with the PCB 12 and the connector 40. The conductive material 22 can also be formed to provide pads or contacts 30 for electrically coupling one or more components or devices 26, 28 to the conductive material 22.

The conductive material 22 can be disposed on one or both of the first major surface 18 and second major surface 20 of substrate 14. Any suitable technique or combination of techniques can be utilized to form the conductive material 22 on the PCB 12. In one or more embodiments, conductive material 22 can be provided on both of the first and second major surfaces 18, 20, and one or more vias or through-holes can be provided through the substrate 14 to electrically couple conductive material 22 disposed on the first major surface 18 with conductive material disposed on the second major surface 20.

The PCB 12 also includes one or more electrical contacts 24 disposed on one or more of the resiliently deflectable elements 16. In general, the electrical contacts 24 are electrically coupled to the conductive material 22 to provide an electrical pathway from one or more components 26, 28 disposed on or associated with the PCB 12 to an associated apparatus or system via the connector 40 as is further described herein. Although depicted as being disposed on each resiliently deflectable element 16, the electrical contacts 24 can be provided on any suitable number of resiliently deflectable elements, e.g., 1, 2, 3, 4, 5, or more deflectable elements. Further, any suitable number of electrical contacts 24 can be disposed on an individual resiliently deflectable element 16.

Electrical contacts 24 can be disposed on the resiliently deflectable elements 16 using any suitable technique or combination of techniques. In one or more embodiments, the electrical contacts 24 can be provided by forming one or more vias through an optional insulating layer 32 that can be provided on the conductive material 22 on the first major surface 18, and/or a second insulating layer 36 provided on conductive material provided on the second major surface 20. Such vias can be formed on one or both of the first major surface 18 and second major surface 20 of the PCB 12.

The electrical contacts 24 can be formed of the same or different material or combination of materials as the conductive material 22. In one or more embodiments, the electrical contacts 24 are disposed on one or both of the first and second major surfaces 18, 20 of the substrate 14 when the conductive material 22 is formed. Further, the electrical contacts 24 can be any suitable dimension and can take any suitable shape or combination of shapes.

As mentioned herein, the print circuit board 12 can also include the insulating layer 32 disposed on the first major surface 18, and the second insulating layer 36 on the second major surface 20 of the substrate 14. Insulating layer 32 is not shown in FIG. 4, for clarity. The insulating layers 32, 36 can include any suitable material or combination of materials that provide electrical insulation or isolation of the conductive material 22. Further, in one or more embodiments, the insulating layers 32, 36 can also protect conductive material 22 from the external environment. In one or more embodiments, one or both of the insulating layers 32, 36 can be disposed such that conductive material 22 is between the insulating layers and the substrate 14.

The PCB 12 can include any other suitable features. For example, the PCB 12 includes a slot or opening 34 that provides access to one or more components as is further described herein. The PCB 12 can include any suitable number of slots or openings for providing access to a component for various testing. As illustrated in FIG. 1, the PCB 12 also includes slot or opening 35 that can provide access to a component, e.g., for hematocrit sampling.

Further in one or more embodiments, the print circuit board 12 can include indicia for aligning the PCB in any suitable manufacturing process. For example, indicia can be provided on one or both surfaces 18, 20 of PCB 12 to align the PCB for providing one or more integrated circuit or electronic components on the PCB as is further described herein. In one or more embodiments, the PCB 12 can include any suitable number of openings that can be utilized to attach the PCB to the casing or enclosure of an apparatus or device.

In one or more embodiments, one or more electronic components or devices can be disposed on the PCB 12 such that they are electrically coupled to conductive material 22. For example, in one or more embodiments, one or more components 26, 28 can be disposed on one or both of the first and second major surfaces 18, 20 of the PCB 12 and electrically coupled to conductive material 22. Any suitable electronic component or components can be disposed on the PCB 12, e.g., integrated circuits (e.g., controllers, switches, memory, etc.), sensors (e.g., resonators, etc.). Such components can be electrically coupled to the conductive material 22 using any suitable technique or combination of techniques. Further, such components can be electrically coupled to the PCB 12 using any suitable conductive material. In one or more embodiments, components 26, 28 can be electrically coupled to conductive material 22 through conductive pads or contacts 30.

In one or more embodiments, each terminal of component 26 can be electrically coupled to a discrete electrical contact 24, and each terminal of component 28 can be electrically coupled to a discrete electrical contact. In one or more alternative embodiments, one or more terminals of an electronic component can be electrically coupled to the same electrical contact. Further, in one or more embodiments, one or more terminals of component 26 can be coupled to the same electrical contact as one or more terminals of component 28.

Figure 6:
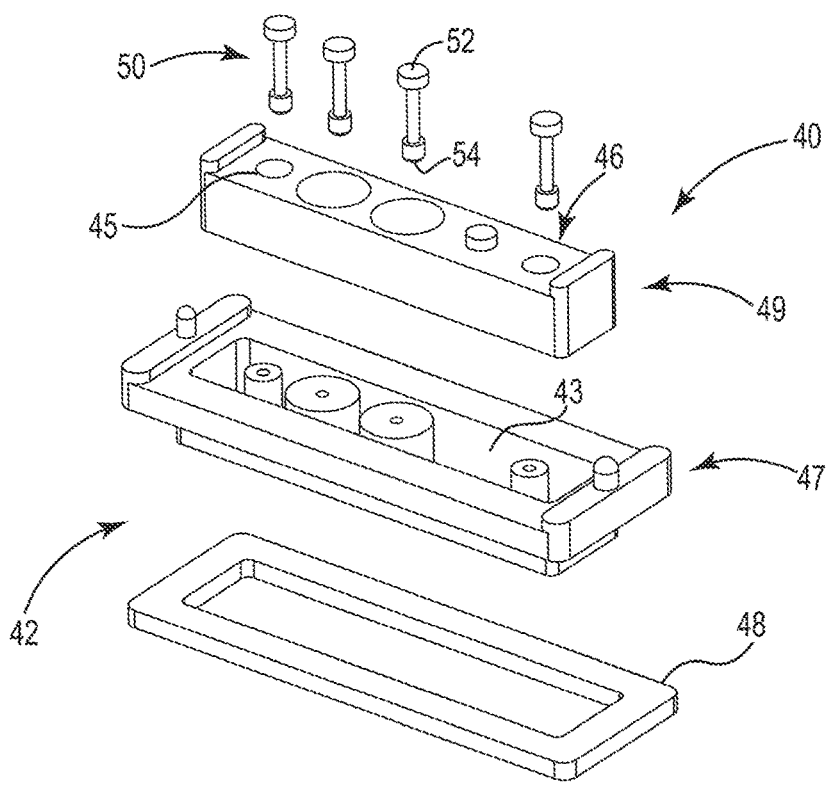
FIG. 6 is a schematic exploded view of a top surface of a connector of the interconnect device of FIG. 1.
Figure 7:
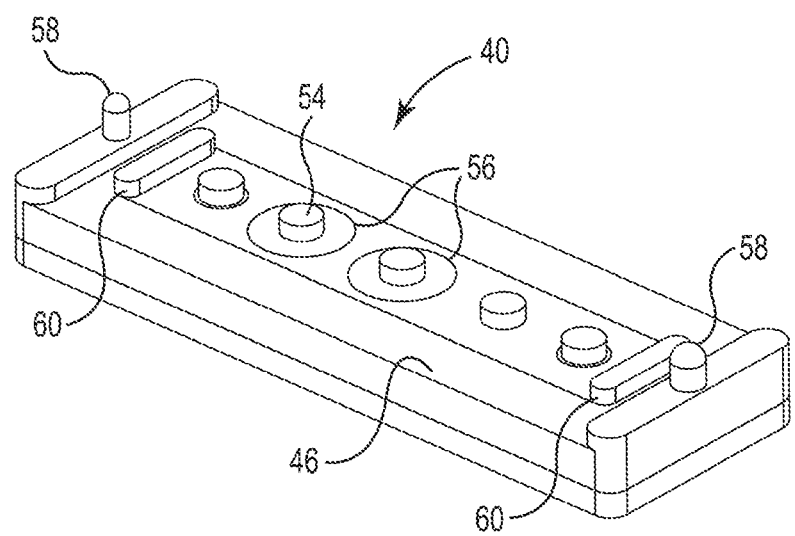
FIG. 7 is a schematic perspective view of a bottom surface of the connector of the interconnect device of FIG. 1.

The interconnect device 10 also includes connector 40. The connector 40 of interconnect device 10 of FIG. 1 is illustrated in greater detail in FIGS. 6-7. FIG. 6 is a schematic exploded view of the connector 40, and FIG. 7 is a schematic perspective view of a bottom surface 46 of the connector 40.

The connector 40 can be disposed within an enclosure or casing of an associated apparatus as is further described herein. For example, the connector 40 can be attached to a PCB or interface of such an associated apparatus using any suitable technique or combination of techniques. In one or more embodiments, posts 58 can be provided on one or both of a top surface 44 and the bottom surface 46 of a body 42 of the device 40. One or more shields 60 can also be provided that can connect the connector 40 to ground on a circuit board of the associated apparatus. The shields 60 can be electrically coupled to one or more connecting pins 50 through a metal layer 57 that contacts such pins. The pins 50 coupled to the shields 60 via metal layer 57 can provide a common ground. Pins 50 that are not electrically coupled to shields 60 can be isolated from the metal layer 57 using cutouts 56.

The connector 40 can also include a body 42 having an opening 45 configured to receive the connecting pin 50. In one or more embodiments, the body 42 can include an opening 45 for each pin 50. In one or more embodiments, the body 42 can include an opening 45 configured to receive two or more pins 50.

As illustrated in FIG. 6, the body 42 can include a first portion 47 and a second portion 49. The first portion 47 can, in one or more embodiments, include an electrically insulative material. And the second portion 49 can, in one or more embodiments, include an electrically conductive material.

The first portion 47 of the body 42 can be configured to receive the second portion 49 such that the second portion sits within a recess 43 in the first portion. The connector 40 can be assembled by placing the second portion 49 within the recess 43 of the first portion 47. Each pin 50 can be positioned in an opening 45 in the body 42. In one or more embodiments, the pin 50 can include two or more parts such that a first part is positioned within the body 42 and the second part is then attached to the first part.

The connector 40 can be configured such that it provides a seal between the connector and the PCB 12 when the connector and the PCB are electrically coupled. For example, connector 40 can include a gasket 48 around a periphery of the body 42 to isolate the electrical connection between the PCB 12 and the connector when they are engaged.

The connector 40 includes one or more connecting pins 50. In one or more embodiments, one or more of the connecting pins 50 can be fixed. As used herein, the phrase "fixed connecting pin" refers to a pin or post that remains fixed in place when contacted with a resiliently deflectable element 16 of the PCB 12 of the interconnect device 10. Although illustrated as including 5 connecting pins 50, the connector 40 can include any suitable number of connecting pins, e.g., 1, 2, 3, 4, 5, or more connecting pins.

The connecting pins 50 can take any suitable shape or combination of shapes. Further, the connecting pins 50 can include any suitable material or combination of materials that provide an electrical pathway from the PCB 12 to an apparatus associated with the connector 40.

The body 42 can take any suitable shape or combination of shapes. In one or more embodiments, the body 42 can include a step to receive a gasket such that the connector 40 is sealed within the associated apparatus. Each connecting pin 50 can include a first end 52 and a second end 54. The first end 52 is configured to contact electrical contact 24 disposed on the resiliently deflectable element 16 of the PCB 12. The second end 54 of the connecting pin 50 is configured to make an electrical connection with a contact or pad of a PCB or other interface of an associated apparatus.

Figure 2:
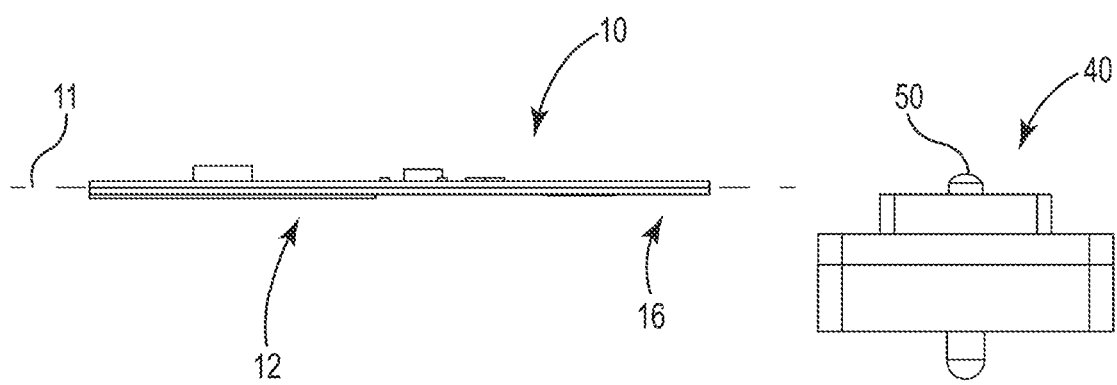
FIG. 2 is a schematic cross-section side view of the interconnect device of FIG. 1.
Figure 3:
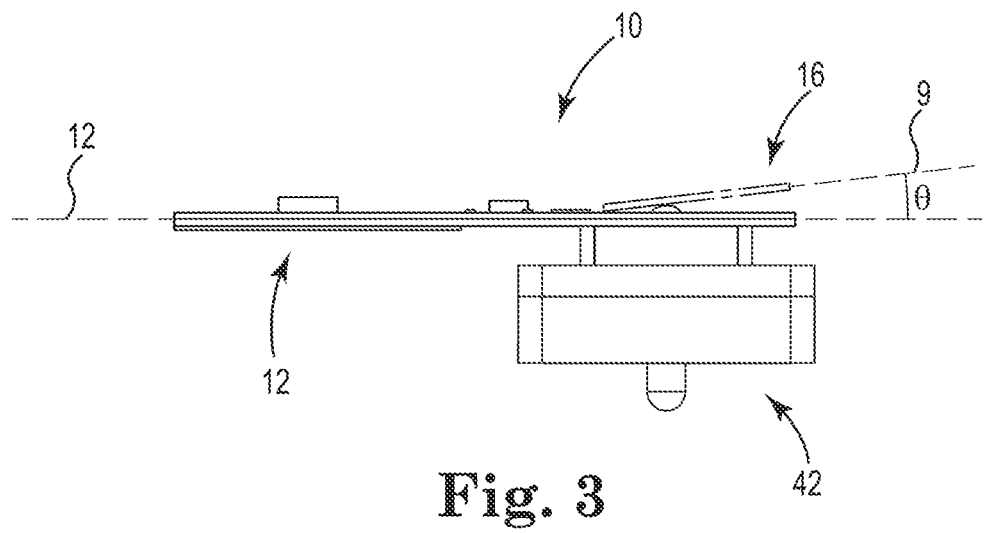
FIG. 3 is a schematic cross-section side view of the interconnect device of FIG. 1.

Each connecting pin 50 is also configured to cause a resiliently deflectable element 16 of the PCB 12 to deflect when the element contacts the pin 50. For example, FIGS. 2-3 are schematic cross-section side views of the interconnect device 10 of FIG. 1. FIG. 2 illustrates the interconnect device 10 when the PCB 12 and the connector 40 are spaced apart. As can be seen in FIG. 2, the resiliently deflectable elements 16 of the PCB 12 are in a non-deflected state such that the resiliently deflectable elements are substantially parallel with a plane 11 of the substrate 14 of the PCB. As used herein, the phrase "substantially parallel" means that a plane containing one or more resiliently deflectable elements forms an angle with the plane 11 of the substrate 14 that is no greater than 5 degrees. In one or more embodiments, the non-deflected states of the resiliently deflectable elements 16 are their relaxed states (i.e., the configuration they assume under no external forces applied by contact with the connecting pins 50 of the connector 40). According to their resilient nature, the elements 16 may return substantially to their relaxed states after being deflected.

As seen in FIG. 3, the connecting pins 50 are configured to cause one or more resiliently deflectable elements 16 to deflect when the element contacts the pin such that the resiliently deflectable element forms any suitable angle $\theta$ with the plane of the substrate 14 of the PCB 12, thereby electrically coupling the PCB to the connector 40. For example, in one or more embodiments, the pin 50 is configured to cause one or more resiliently deflectable elements 16 to deflect such that they form an angle $\theta$ of greater than 5°, greater than 10°, or greater than 15° with the plane 11 of the substrate 14 of the PCB 12. In one or more embodiments, the angle $\theta$ between one or more of the deflected resiliently deflectable elements 16 and the plane 11 of the substrate 14 is no greater than 90°, no greater than 70°, no greater than 60°, or no greater than 50°. In one or more embodiments, the connecting pin 50 can cause the resiliently deflectable element 16 to deflect in a range of angles $\theta \pm 90°$, $\pm 80°$, $\pm 70°$, $\pm 60°$, $\pm 50°$, $\pm 40°$, $\pm 30°$, $\pm 20°$, $\pm 10°$, or $\pm 5°$. In general, the deflection caused by the connecting pin 50 is sufficient to electrically couple the electrical contact 24 with the connecting pin without causing unwanted strain on the PCB 12, e.g., without causing cracking or fracturing of the PCB. While not wishing to be bound by any particular theory, the deflection of the resiliently deflectable element 16 provides sufficient force between the electrical contact 24 and the pin 50 such that electrical coupling is maintained between the PCB 12 and the connector 40.

Any suitable amount of force can be provided by the pin 50 to the resiliently deflectable element 16. In one or more embodiments, each pin 50 can provide at least 2 oz of force to an associated element 16. In one or more embodiments, each pin 50 can provide no greater than 10 oz of force to an associated element 16. In one or more embodiments, each pin 50 can be provide 2-5 oz of force to an associated element 16.

Although not shown in FIGS. 1-7, the interconnect device 10 can include any suitable alignment structure or mechanism such that the electrical contact 24 of the PCB 12 can be aligned with a pin 50 of the connector 40.

Figure 8:
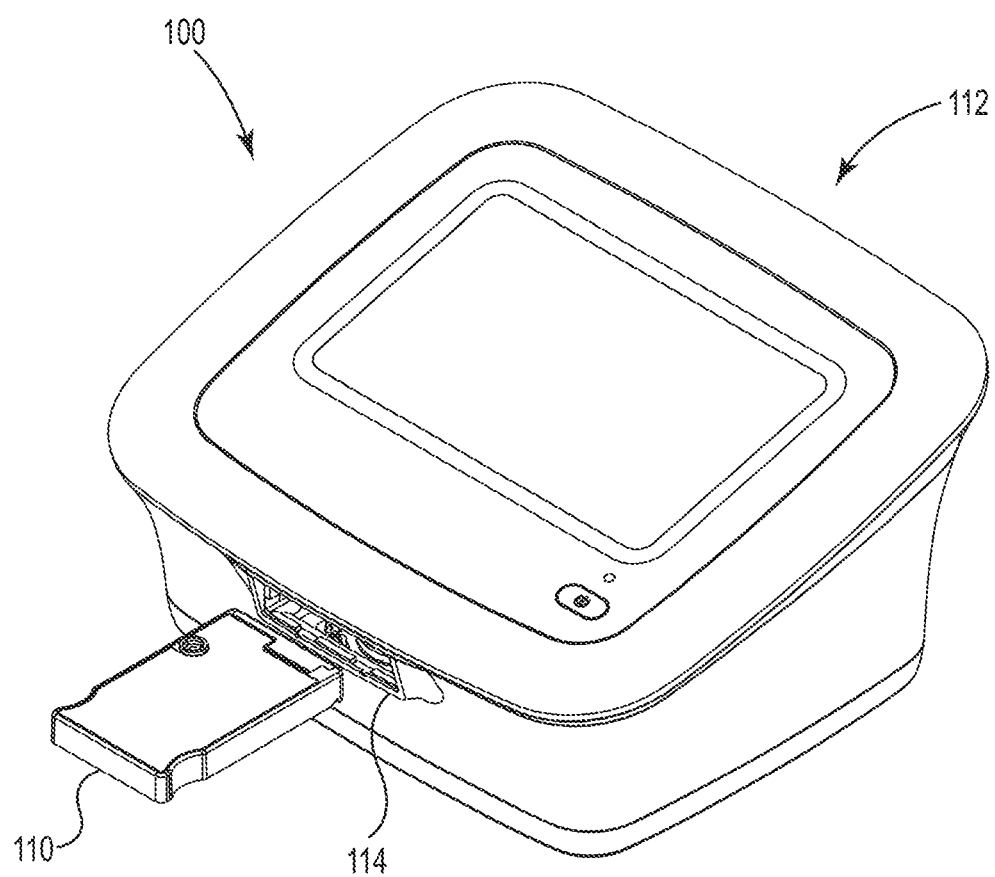
FIG. 8 is a schematic perspective view of one embodiment of a resonator sensor system.

In general, the interconnect device 10 can be utilized with any suitable devices, apparatuses, components, or systems to provide an electrical coupling between two or more apparatuses. For example, FIG. 8 is a schematic perspective view of a resonator sensor system 100. In one or more embodiments, the resonator sensor system 100 can be used for measuring binding kinetics of an interaction of an analyte material present in a fluid sample. The system 100 includes a resonator sensor module 110 and an associated measurement apparatus 112 that is configured to receive the module at a module port 114.

As illustrated in FIG. 8, system 100 is a portable system that can be used for point-of-need diagnostic testing in the field. Although the system 100 is depicted as being portable, in one or more embodiments, the system can be utilized on a laboratory bench or in a more permanent configuration. Although not shown in FIG. 8, the system 100 can include devices and circuitry for connection to the internet or otherwise transferring information, such as one or more USB ports, wireless connection, or the like. In one or more embodiments, the system 100 is configured with a network interface device and associated firmware/drivers, which enable the system to automatically initiate a query over a network to obtain calibration constants for the specific sensor module. This embodiment eliminates the need for maintaining calibration data locally. Instead, when a new resonator sensor module is attached, the instrument determines the serial number associated with the particular sensor module (using RFID, bar code scanning, etc.), and uses that information to form its query. The database having specific sensor calibration data may be stored on a server located at the laboratory facility, or remotely (e.g., at the manufacturer's facility), in which case the network over which the query is placed is a wide area network (WAN) such as the Internet.

The module port 114 is configured to receive the resonator sensor module 110. In one or more embodiments, the module port 114 includes an alignment structure (not shown) that aligns the resonator sensor module 110 such that a contact (e.g., contact 24 of FIG. 1) of a resiliently deflectable element (e.g., element 16 of FIG. 1) is aligned with a connecting pin (e.g., pin 50 of FIG. 1) of a connector (e.g., connector 40 of FIG. 1). Any suitable alignment structure can be utilized to align the resonator sensor module 110 with the measurement apparatus 112.

Figure 9:
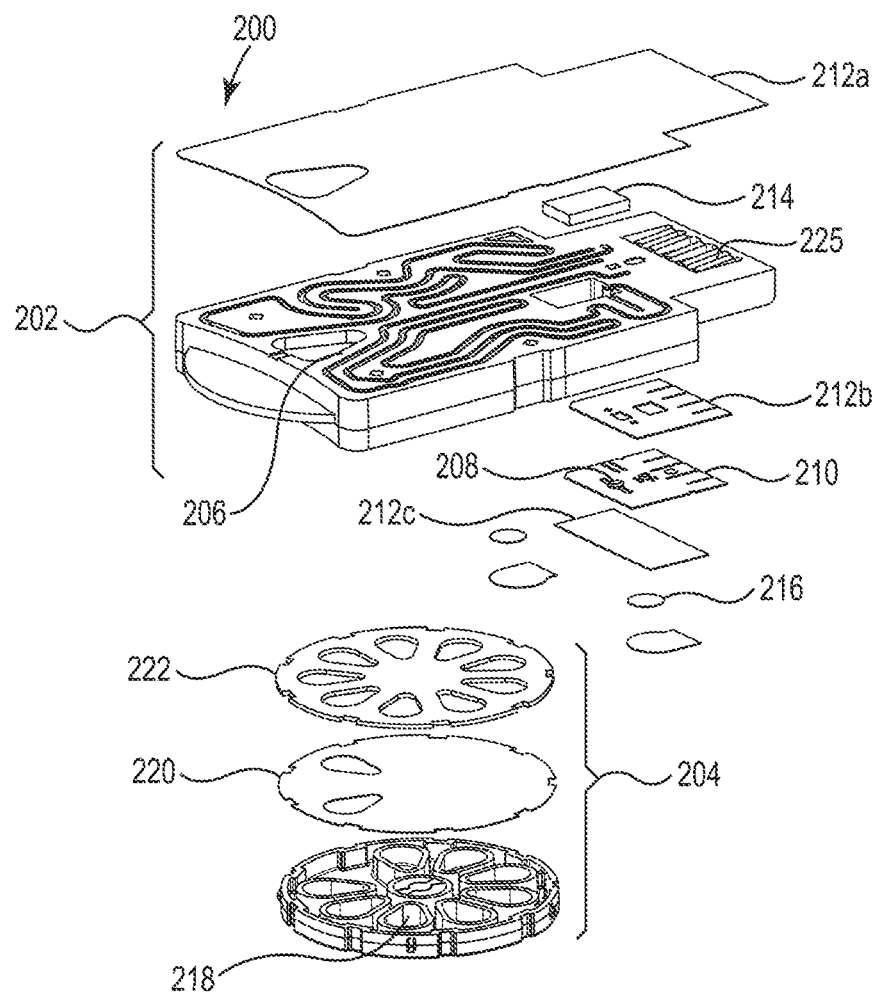
FIG. 9 is a schematic exploded view of one embodiment of a resonator sensor module.
Figure 10:
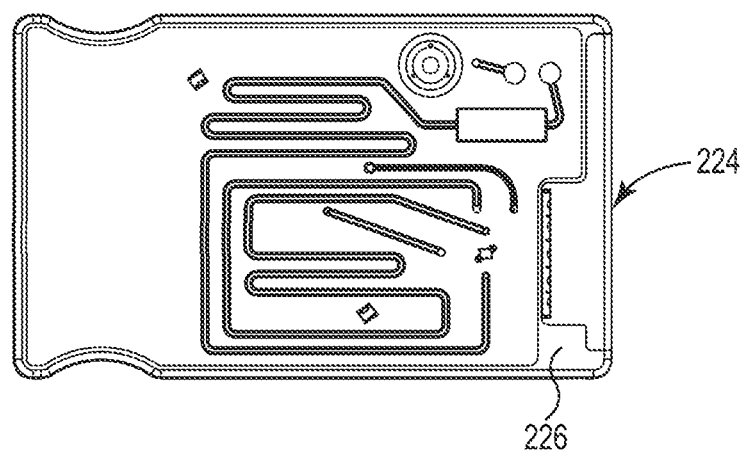
FIG. 10 is a schematic plan view of a top surface of the resonator sensor module of FIG. 9.
Figure 11:
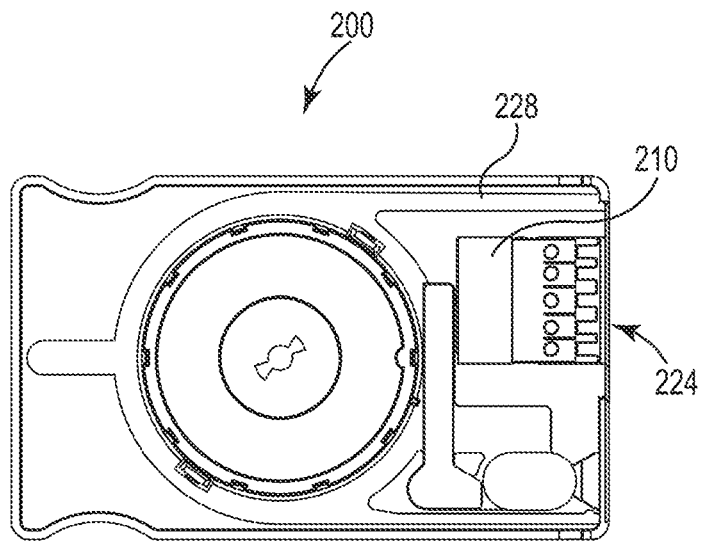
FIG. 11 is a schematic plan view of a bottom surface of the resonator sensor module of FIG. 9.

The resonator sensor module 110 can include any suitable resonator sensor module or device, e.g., the resonator sensor modules described in cofiled PCT Patent Application No. PCT/US2014/039400 to Webster, entitled TWO PART ASSEMBLY. For example, FIGS. 9-11 are schematic views of one embodiment of a resonator sensor module 200 that can be utilized with system 100 of FIG. 8. FIG. 9 is a schematic exploded view of the resonator sensor module 200, FIG. 10 is a schematic cross-section plan view of a top surface 226 of the module, and FIG. 11 is a schematic cross-section plan view of a bottom surface 228 of the module.

The resonator sensor module 200 includes a first portion 202 and a second portion 204. The first portion 202 includes a channel 206 and a sensor 208 on a printed circuit board (PCB) 210. The PCB 210 can include any suitable PCB, e.g., PCB 12 of interconnect device 10 of FIG. 1. Further, module 200 can include any suitable sensor or sensors 208.

For example, in one or more embodiments, the sensor 208 can include one or more resonators. The resonators described herein can be thin-film resonators (TFRs). Thin film resonators can include a thin layer or film of piezoelectric material deposited on a substrate, rather than using, for example, AT-cut quartz. The piezoelectric films typically have a thickness of less than about 5 micrometers, such as less than about 2 micrometers, and may have thicknesses of less than about 100 nanometers. In one or more embodiments, thin-film resonators may be preferred because of their high resonance frequencies and the theoretically higher sensitivities. Depending on the applications, a thin-film resonator can be formed to support either longitudinal or shear bulk-acoustic wave resonant modes. In one or more embodiments, the resonator is formed to support shear bulk-acoustic wave resonant modes as they can be more suitable for use in a liquid sample.

Additional details regarding sensor devices and systems that may employ TFRs are described, for example, in U.S. Pat. No. 5,932,953 issued Aug. 3, 1999 to Drees et al., entitled METHOD AND SYSTEM FOR DETECTING MATERIAL USING PIEZOELECTRIC RESONATORS; and U.S. Pat. No. 8,409,875 issued Apr. 2, 2013, to Johal et al., entitled MEASUREMENT OF BINDING KINETICS WITH A RESONATING SENSOR.

TFR sensors may be made in any suitable manner and of any suitable material. By way of example, a resonator may include a substrate such as a silicon wafer or sapphire, a Bragg mirror layer or other suitable acoustic isolation means, a bottom electrode, a piezoelectric material, and a top electrode.

Any suitable piezoelectric material may be used in a TFR. Examples of suitable piezoelectric substrates include lithium tantalate ($LiTaO_3$), lithium niobate ($LiNbO_3$), Zinc Oxide (ZnO), aluminum nitride (AlN), plumbum zirconate titanate (PZT) and the like.

Electrodes may be formed of any suitable material, such as aluminum, tungsten, gold, titanium, molybdenum, or the like. Electrodes may be deposited by vapor deposition or may be formed by any other suitable process.

In one or more embodiments, the resonator 208 of module 200 can include a sensing resonator that includes binding sties for an analyte material, and a reference resonator that lacks any binding sites for the analyte material as if further described in PCT Patent Application No. PCT/US2014/039400 to Webster, entitled TWO PART ASSEMBLY.

In one or more embodiments, the module 200 can include back-to-back PCB configurations utilizing two substantially different PCBs. In one approach, the resonator on one PCB is situated off-center while the resonator on the other PCB is centered. In this configuration, the reference and sensing resonators can still have sufficient distance there-between to reduce cross talk between the two resonators. In another aspect of the present disclosure, the resonators on the two PCBs are constructed such that the back-to-back PCB configuration results in the reference and sensing resonators being directly opposed.

In one or more embodiments, the sensing resonator is coated with a different material than a reference resonator depending upon the material to be detected. By varying the coating on the resonators, the disclosed systems can allow universal use for various diagnostic testing of chemical and/or biological materials without changing any of the other system structural components. Sensors for resonance shift detection of chemical and/or biological materials effectively allow fast response times for the detection of the respective chemical and/or biological material, in the field detection capabilities, small sample sizes, minimally trained individuals, low direct and indirect costs, and electronically transmittable data.

Although not necessarily easily visible in FIG. 9, the PCB 210 includes a slot (e.g., slot 34 of PCB 12) in which at least the piezoelectric layer of the sensor 208 sits. The first portion 202 also includes three different adhesive films 212a, 212b, and 212c. The adhesive films 212a, 212b, and 212c along with the channel 206 and at least a portion of the PCB 210 and sensor 208 form the fluidic pathway. This particular exemplary sensor assembly also includes a waste wick 214, which is within or in fluid communication with the fluidic pathway. The waste wick 214 can function to contain overflow fluid from the fluidic channel. This particular exemplary sensor assembly also includes at least one, and in this embodiment two hydrophobic vents 216. The hydrophobic vents 216 function to provide a liquid stop for use in metering and to prevent liquid ingress into the instrument when using an external pump.

The second portion 204 is circular and is configured to be rotated around a central point. The second portion 204 includes eight (8) wells (illustrated by well 218). The wells 218 in this exemplary embodiment have a teardrop shape. Shapes such as a teardrop shape may provide an advantageous use of space, but it should also be noted that other shapes, such as circular shapes for example could also be suitable. It should also be noted that there are portions of the housing of the second portion that do not include wells. The portion without a well can be utilized to have a position for the introducer upon assembly of the first and second portion. It is noted that the empty well for the introducer to be placed in upon initial assembly cannot be the sample introduction well because it has to be accessible for introduction of the sample. It should also be noted that this function could be served by an additional empty well (instead of a void). In this particular embodiment, the wells are sealed with one portion or piece of material, e.g., a seal 220. In this exemplary embodiment, the seal 220 is made of a metal foil. This particular embodiment of the seal 220 includes two openings that are positioned over the voids. These openings can allow advantageous assembly with introducer placement.

This particular embodiment of a sensor assembly 200 also includes a gasket layer 222. The gasket layer 222 can be made of any material that is somewhat compliant (to allow for a gasket type of function), and in some embodiments, the gasket material does not absorb a sufficient amount of liquid. The gasket layer 222 can be advantageous because it can function to seal the wells once they have been punctured by the introducer. In some embodiments, the gasket layer 222 can be attached to (via adhesive for example), or formed integrally with the seal 220.

The resonator sensor module 200 may include various one or more flow paths in fluid communication with the resonator across which a fluid sample containing analyte may flow. The flow paths may be in communication with one or more reagents that may be drawn across the surface of the resonator, with or without the analyte. The resonator may be associated with the PCB 210. The resonator sensor module 200 also includes an interconnect device 224 (e.g., PCB 12 of interconnect device 10 of FIG. 1) for electrical coupling to an associated apparatus or system, e.g., apparatus 112 of FIG. 8.

Any suitable technique or combination of techniques can be used with the system 100 of FIG. 8 for detection of test material. For example, a bulk-acoustic wave piezoelectric resonator can be used as a sensor to detect an analyte. Such resonators may be included in the resonator sensor modules described herein, e.g., module 200. The resonator typically includes a planar layer of piezoelectric material bounded on opposite sides by two respective metal layers that form the electrodes of the resonator. The two surfaces of the resonator are free to undergo vibrational movement when the resonator is driven by a signal within the resonance band of the resonator. When the resonator is used as a sensor, at least one of its surfaces is adapted to provide binding sites for the material being detected. The binding of the material on the surface of the resonator alters the resonant characteristics of the resonator, and the changes in the resonant characteristics are detected and interpreted to provide quantitative information regarding the material being detected.

By way of example, such quantitative information may be obtained by detecting a change in the insertion phase shift of the resonator caused by the binding of the material being detected on the surface of the resonator. Such sensors differ from those that operate the resonator as an oscillator and monitor changes in the oscillation frequency. Rather, such sensors insert the resonator in the path of a signal of a pre-selected frequency and monitor the variation of the insertion phase shift caused by the binding of the material being detected on the resonator surface.

Any suitable molecular recognition component may be bound to the surface of a resonator. The molecular recognition component preferably selectively binds to the analyte of interest. By way of example, the molecular recognition component may be selected from the group consisting of nucleic acids, nucleotides, nucleosides, nucleic acids analogues such as PNA and LNA molecules, proteins, peptides, antibodies including IgA, IgG, IgM, IgE, lectins, antibody fragments, enzymes, enzymes cofactors, enzyme substrates, enzymes inhibitors, receptors, ligands, kinases, Protein A, Poly U, Poly A, Poly lysine, triazine dye, boronic acid, thiol, heparin, polysaccharides, coomassie blue, azure A, metal-binding peptides, sugar, carbohydrate, chelating agents, prokaryotic cells and eukaryotic cells.

The module interface 224 can include any suitable structure such that the interface can connect the module 200 to an associated apparatus. In one or more embodiments, the interface 224 can include one or more resiliently deflectable tabs or fingers 225 formed in the first portion 202 of the module 200 such that the module is configured to engage a connector (e.g., connector 40 of FIG. 1) of an associated device (e.g., measurement apparatus 112). The fingers 225, in one more embodiments, are configured to interlock with the casing of the connector of the associated device such that the module is securely connected to the associated device.

Returning to FIG. 8, the system 100 includes measurement apparatus 112. The apparatus 112 is operatively coupled to the resonator sensor module 110 through an interconnect device, e.g., interconnect device 10 of FIG. 1. The interconnect device can include the module interface (e.g., module interface 224 of module 200) of the resonator sensor module 110 and a connector (e.g., connector 40) disposed within apparatus 112. The interconnect device can be sealed such that is protected from the environment when the resonator sensor module 110 is connected to the apparatus 112 via module port 114. Once detection and testing is completed, the module 110 can be detached from apparatus 112 and either reconditioned for additional testing or disposed of.

In some embodiments, the apparatus 112 can include a data storage device such as a ROM or flash EEPROM. The data storage device may serve to set up the instrument for specific market applications by including software or identification information that allows the instrument to understand the particular use of the system 100 as it relates to the resonator sensor module 110. For instance, the read-only memory may contain basic information or algorithmic instructions for the interpretive logic of the instrument that relates to the output signal of the module 110, which may serve to limit the system 100 to specific applications, such as limited only to use in one of: veterinary applications, toxicology applications, drugs of abuse applications; GMO grain applications, for example.

The data storage device can also contain sensor-type specific information such as the general frequency range or approximate resonance frequency of one or more resonators of the module 110 as determined during post-production testing. This information could, for example, reduce sensor detection and calibration setup time when a new sensor is coupled to an instrument. In a related embodiment, the data storage device contains lookup tables of calibration correction constants that are indexed by lookup codes individually determined for the sensors at the factory. In various other embodiments, the lookup code may be supplied via printed label, barcode label, or using a RFID tag.

Figure 12:
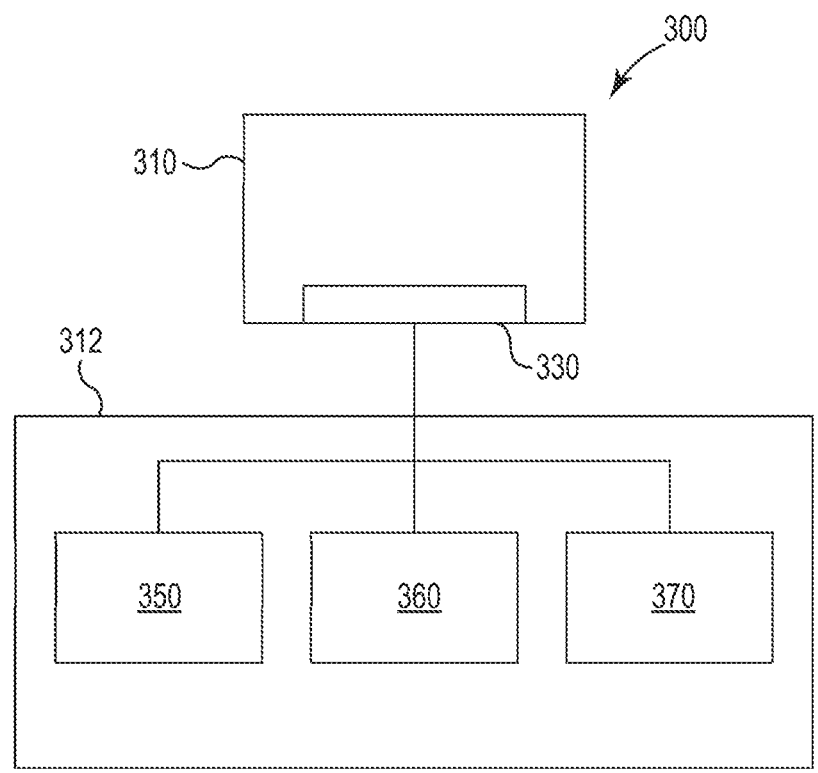
FIG. 12 is a schematic diagram of another embodiment of a resonator sensor system.

In one or more embodiments, the module 110 can include a read-only memory (ROM) or small flash device having its own specific calibration constants specific to the individual sensor module. This data could be supplied based on factory calibration performed on a representative sample taken from the manufactured lot in which the individual module 110 was fabricated. The various embodiments of resonator sensor modules described herein can be used with any suitable measurement apparatus to provide a resonator sensor system for measuring the binding kinetics of an interaction of an analyte material present in a fluid sample, e.g., the apparatuses described in U.S. Pat. No. 8,409,875. For example, FIG. 12 is a schematic diagram of one embodiment of a system 300 that includes a resonator sensor module 310 and a measurement apparatus 312. The resonator sensor module 310 can include any resonator sensor module described herein, e.g., module 200 of FIGS. 9-11. Module 310 includes a module interface 330.

As illustrated, the measurement apparatus 312 is operatively coupled to the resonator sensor module 310 through the module interface 330. Any suitable interconnect device can be utilized to operatively couple the measurement apparatus 312 to the module 310, e.g., interconnect device 10 of FIG. 1.

The apparatus 312 includes actuation circuitry 350, measurement circuitry 360, and a controller 370 operatively coupled to the actuation and measurement circuitry.

The actuation circuitry 350 is configured to drive a sensor (e.g., sensor 26 of FIG. 4) of the module 310 into an oscillating motion as is further described herein. The actuation circuitry 350 can include any suitable device or devices to drive the resonators in this manner, e.g., synthesizers, independent current sources, independent voltage sources, voltage controlled oscillators (VCO), backward wave oscillators (BWO), and combinations thereof.

The actuation circuitry 350 is configured to drive the one or more sensors (e.g., resonators) at any suitable frequency or frequencies. In one or more embodiments, the actuation circuitry 350 is configured to drive one or more sensors at its resonant frequency. In some embodiments, the actuation circuitry 350 is configured to drive one sensor at a first frequency and a second sensor at a second frequency. For example, the resonator sensor module 310 can include one or more sensing resonators and one or more reference resonators. The actuation circuitry 350 would, therefore, be configured to drive the one or more sensing resonators at a first frequency and the one or more reference resonators at a second frequency. In some embodiments, the first frequency is substantially equal to the second frequency. In other embodiments, the first frequency is different from the second frequency.

The system 300 also includes measurement circuitry 360 configured to measure one or more resonator output signals representing a resonance characteristic of the oscillating motion of the one or more sensors of module 310. Measurement circuitry 360 can include any suitable device or devices to measure these output signals, e.g., gain/phase detectors, amplifiers, filters, analog-to-digital circuits (ADCs), digital-to-analog circuits (DACs), mixers, directional couplers, RF receivers, and combinations thereof.

Also included in the measurement apparatus 312 of the embodiment illustrated in FIG. 12 is a controller 370. The controller 370 is operatively coupled to the actuation circuitry 350 and measurement circuitry 360. The controller 370 can include any suitable device or devices, e.g., microprocessors, microcontrollers, field programmable gate arrays (FPGAs), analog control circuits, application specific integrated circuits (ASICs), computers, and combinations thereof. In some embodiments, the controller 370 can include a combination of hardware and software, such as by a microprocessor system and a set of instructions to implement the controller's functionality. In one or more embodiments, the controller 370 can be implemented as a combination of the two, with certain functions facilitated by hardware alone, and other functions facilitated by a combination of hardware and software. A variety of suitable microprocessor systems may be utilized including, without limitation, one or more microcontrollers, one or more digital signal processors, and the like, along with appropriate interfacing circuitry, data storage, power conditioning system, etc., as needed to implement the controller's functionality.

In one or more embodiments, the controller 370 is configured to perform various measurement functions as are described further in U.S. Pat. Nos. 5,932,953 and 8,409,875. For example, in some embodiments, the controller 370 is configured to detect introduction of a fluid sample into contact with at least one of the one or more sensing resonators of module 310 based on detection of a characteristic change in the sensing resonator output signal, e.g., the resonant frequency of the one or more sensing resonators. And in some embodiments, the controller 370 is configured, in response to the detection of the introduction of the fluid sample, to initiate measurement of the binding kinetics of the analyte material to the at least one of the one or more sensing resonators.

In one or more embodiments, the controller 370 is further configured to monitor the one or more resonator output signals from a time reference based on the time of occurrence of the characteristic change in the output signal. Further, in some embodiments, the controller 370 is configured to detect a step change in a resonant characteristic of at least one of the one or more sensing resonators and at least one of the one or more reference resonators selected from the group consisting of: a frequency, a reflection or transmission phase angle, a reflection or transmission amplitude, or any combination thereof. And in some embodiments, the controller 370 is further configured to determine a measure of concentration of the analyte in the fluid sample based on the binding kinetics.

The controller 370 is further configured to send a control signal to a device (e.g., device 28 of FIG. 4). For example, the controller 370 can be configured to send a control signal to a switch to position the switch in either a first position or a second position. In one or more embodiments, the first position of the switch operatively couples a sensing resonator and the module interface 330, and the second position operatively couples a reference resonator and the module interface. The control signal is provided to the switch via the module interface. Any suitable switches and circuitry can be utilized to operatively couple the module interface 330 and one or more resonators of the resonator sensor module 310, e.g., those described in PCT Patent Application No. PCT/US2014/039291 to Tischer, entitled RESONATOR SENSOR MODULE AND SYSTEM AND METHOD USING SAME.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. An interconnect device, comprising:
   a printed circuit board (PCB) comprising:
      a substrate forming a resiliently deflectable element, wherein the resiliently deflectable element comprises a peripheral portion of the substrate that comprises a slot formed in the substrate that defines the resiliently deflectable element;
      a conductive material disposed on the substrate; and
      an electrical contact disposed on the resiliently deflectable element and electrically coupled to the conductive material; and
   a connector comprising a connecting pin configured to electrically couple with the electrical contact of the resiliently deflectable element of the PCB and cause the resiliently deflectable element to deflect when the resiliently deflectable element contacts the connecting pin.

2. The device of claim 1, wherein the connector further comprises a body having an opening configured to receive the connecting pin.

3. The device of claim 2, wherein the connecting pin is fixed.

4. The device of claim 2, wherein the connector further comprises a gasket positioned around a periphery of the body.

5. The device of claim 1, wherein the PCB further comprises an insulating layer disposed such that the conductive material is between the insulating layer and the substrate.

6. The device of claim 5, wherein the electrical contact comprises a via formed through the insulating layer to the conductive material.

7. The device of claim 1, wherein the conductive material and the electrical contact are disposed on a first major surface of the substrate of the PCB.

8. The device of claim 1, wherein the conductive material is disposed on a second major surface of the PCB, and the electrical contact is disposed on a first major surface of the substrate, wherein the electrical contact is electrically coupled to the conductive material through one or more vias that extend through the substrate.

9. The device of claim 1, further comprising an electronic component disposed on a first major surface of the PCB and electrically coupled to the conductive material.

10. The device of claim 9, wherein the electronic component comprises a sensor.

11. The device of claim 10, wherein the electronic component comprises a resonator.

12. The device of claim 11, wherein the resonator comprises a bulk acoustic wave resonator.

13. The device of claim 12, wherein the bulk acoustic resonator comprises a shear-mode bulk acoustic wave resonator.

14. The device of claim 11, wherein the device comprises a second resonator and a switch that operatively couples the resonator and the second resonator to the conductive material.

15. A resonator sensor module comprising a module interface and a resonator electrically coupled to the module interface, wherein the module interface comprises a printed circuit board (PCB) comprising:
   a substrate forming a resiliently deflectable element, wherein the resiliently deflectable element comprises a peripheral portion of the substrate that comprises a slot formed in the substrate that defines the resiliently deflectable element;

a conductive material disposed on the substrate; and an electrical contact disposed on the resiliently deflectable element and electrically coupled to the conductive material;

wherein the resonator is electrically coupled to the conductive material.

16. The module of claim 15, wherein the resonator comprises a bulk acoustic wave resonator.

17. The module of claim 15, wherein the resonator comprises a sensing resonator comprising binding sites for an analyte material and a reference resonator that lacks binding sites for the analyte material.

18. The module of claim 17, wherein the module further comprises a switch comprising a first position that operatively couples the sensing resonator and the module interface and a second position that operatively couples the reference resonator and the module interface.

19. A resonator sensor system for measuring binding kinetics of an interaction of an analyte material present in a fluid sample, comprising:

the resonator sensor module of claim 15; and a measurement apparatus operatively coupled to the resonator sensor module through an interconnect device comprising the module interface of the resonator sensor module and a connector of the measurement apparatus, wherein the measurement apparatus comprises:

actuation circuitry configured to drive the resonator into an oscillating motion;

measurement circuitry configured to measure a resonator output signal representing a resonance characteristic of the oscillating motion of the resonator; and a controller operatively coupled to the actuation and measurement circuitry.

20. The system of claim 19, wherein the connector electrically couples the measurement apparatus to the module interface of the resonator sensor module, the connector comprising a connecting pin configured to electrically couple with the electrical contact of the resiliently deflectable element of the PCB and cause the resiliently deflectable element to deflect when the element contacts the connecting pin.

* * * * *